(12) United States Patent
Someya et al.

(10) Patent No.: US 10,588,525 B2
(45) Date of Patent: Mar. 17, 2020

(54) MULTI-POINT PROBE, ELECTRONIC CONTACT SHEET FOR CONFIGURING THE SAME, MULTI-POINT PROBE ARRAY, AND METHOD OF MANUFACTURING THE SAME

(71) Applicant: JAPAN SCIENCE AND TECHNOLOGY AGENCY, Kawaguchi-shi, Saitama (JP)

(72) Inventors: Takao Someya, Tokyo (JP); Tsuyoshi Sekitani, Tokyo (JP); Shinri Sakai, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 1072 days.

(21) Appl. No.: 14/892,485

(22) PCT Filed: May 21, 2014

(86) PCT No.: PCT/JP2014/063467
§ 371 (c)(1),
(2) Date: Nov. 19, 2015

(87) PCT Pub. No.: WO2014/189077
PCT Pub. Date: Nov. 27, 2014

(65) Prior Publication Data
US 2016/0100768 A1    Apr. 14, 2016

(30) Foreign Application Priority Data

May 21, 2013  (JP) .................................. 2013-107229

(51) Int. Cl.
*A61B 5/04*    (2006.01)
*A61B 5/0492*  (2006.01)
(Continued)

(52) U.S. Cl.
CPC ........ *A61B 5/04001* (2013.01); *A61B 5/0478* (2013.01); *A61B 5/0492* (2013.01);
(Continued)

(58) Field of Classification Search
CPC ..... A61B 5/04; A61B 5/04001; A61B 5/0402; A61B 5/0408; A61B 5/042; A61B 5/0422;
(Continued)

(56) References Cited

U.S. PATENT DOCUMENTS 6,024,702 A * 2/2000 Iversen ................ A61B 5/0422
600/378
6,210,339 B1 * 4/2001 Kiepen ................ A61B 5/0215
600/372

(Continued)

FOREIGN PATENT DOCUMENTS

CN    86102810 A    11/1986
CN    101337110 A    1/2009
(Continued)

OTHER PUBLICATIONS

Lian, et al., Computational Study for Stimulating Mechanism and the Optimal Geometry of Microelectrode in Deep-Brain Stimulation, Journal of Xi'an Jiaotong University, Dec. 2008, vol. 42, No. 12, pp. 1537-1540 (4 pp., 9 pp. English translation), Xi'an, China.
(Continued)

*Primary Examiner* — Eun Hwa Kim
(74) *Attorney, Agent, or Firm* — Amster, Rothstein & Ebenstein LLP

(57) ABSTRACT

Provided is a multi-point probe which is formed of a tubular laminate which is configured by winding an electronic contact sheet including a sheet-shaped insulating base material, a plurality of electronic contacts which are arranged to be separated from each other in a column shape on the
(Continued)

sheet-shaped insulating base material, and a plurality of wirings which are connected to each of the electronic contacts on the sheet-shaped insulating base material from a first end towards a second end and laminating the electronic contact sheet to have multiple layers, in which the electronic contacts are not covered with the sheet-shaped insulating base material and are exposed, and the wiringsther than a wiring on the uppermost layer are laminated so that at least some parts thereof are covered with the sheet-shaped insulating base material.

10 Claims, 11 Drawing Sheets

(51) Int. Cl.
  *A61B 5/0478* (2006.01)
  *A61N 1/05* (2006.01)
  *A61B 5/00* (2006.01)

(52) U.S. Cl.
  CPC .......... *A61B 5/6868* (2013.01); *A61N 1/0526* (2013.01); *A61N 1/0551* (2013.01); *A61B 2562/0217* (2017.08); *A61B 2562/043* (2013.01); *A61B 2562/125* (2013.01); *A61N 1/0502* (2013.01)

(58) Field of Classification Search
  CPC .. A61B 5/6852–6858; A61B 2562/164; A61B 2562/166; A61N 1/0472; A61N 1/0476; A61N 1/048; A61N 1/0488; A61N 1/05; A61N 1/0526; A61N 1/056
  See application file for complete search history.

(56) References Cited

U.S. PATENT DOCUMENTS

| | | | | |
|---|---|---|---|---|
| 2003/0018243 | A1* | 1/2003 | Gerhardt | A61B 5/0059 600/322 |
| 2007/0219551 | A1* | 9/2007 | Honour | A61B 5/0422 606/41 |
| 2008/0140152 | A1* | 6/2008 | Imran | A61N 1/0553 607/46 |
| 2009/0143651 | A1* | 6/2009 | Kallback | A61B 5/02007 600/301 |
| 2009/0240249 | A1 | 9/2009 | Chan et al. | |
| 2010/0204560 | A1 | 8/2010 | Salahieh et al. | |
| 2010/0222668 | A1* | 9/2010 | Dalke | A61K 51/0491 600/424 |
| 2011/0047789 | A1* | 3/2011 | Lyders | H05K 1/118 29/745 |
| 2011/0093052 | A1 | 4/2011 | Anderson et al. | |
| 2011/0237921 | A1 | 9/2011 | Askin, III et al. | |
| 2012/0157804 | A1* | 6/2012 | Rogers | A61B 5/0422 600/345 |
| 2013/0018247 | A1 | 1/2013 | Glenn et al. | |
| 2013/0109986 | A1 | 5/2013 | Liu et al. | |

FOREIGN PATENT DOCUMENTS

| | | |
|---|---|---|
| CN | 102323857 A | 1/2012 |
| JP | H08-504333 A | 5/1996 |
| JP | 2000-237155 A | 9/2000 |
| JP | 2000-325320 A | 11/2000 |
| JP | 2001-157669 A | 6/2001 |
| JP | 2004-520898 A | 7/2004 |
| JP | 2009-254902 A | 11/2009 |
| JP | 4406697 B2 | 2/2010 |
| JP | 2010-516353 A | 5/2010 |
| JP | 2010-200875 A | 9/2010 |
| JP | 2011-030678 A | 2/2011 |
| JP | 2012-010978 A | 1/2012 |
| JP | 2012-130519 A | 7/2012 |
| JP | 2013508016 A | 3/2013 |
| JP | 2013-514146 A | 4/2013 |
| WO | 94/07412 A1 | 4/1994 |
| WO | 2008/024857 A2 | 2/2008 |
| WO | 2008/092246 A1 | 8/2008 |
| WO | 2011/051775 A2 | 5/2011 |
| WO | 2011/084450 A1 | 7/2011 |

OTHER PUBLICATIONS

State Intellectual Property Office of People's Republic of China Office Action and Search Report for Chinese Application No. 201480028978.7 (5 pp., 5 pp. English translation of cover page and search report), dated Feb. 14, 2017.

Japanese Patent Office, Office Action in Japanese Application No. 2013-107229 (2 pp., 2 pp. English translation), dated Apr. 18, 2017.

European Patent Office, "Extended European Search Report," issued in European Patent Application No. 14 801 868.2, which is a European Counterpart of U.S. Appl. No. 14/892,485 dated Dec. 14, 2016, 8 pages.

Tsuyoshi Sekitani et al., "Flexible organic transistors and circuits with extreme bending stability", Nature Materials, vol. 9, pp. 1015-1022 (Dec. 2010).

International Search Report received for PCT Patent Application No. PCT/JP2014/063467 dated Jun. 17, 2014, 4 pages (2 page of English Translation and 2 page of International Search Report).

* cited by examiner

MULTI-POINT PROBE, ELECTRONIC CONTACT SHEET FOR CONFIGURING THE SAME, MULTI-POINT PROBE ARRAY, AND METHOD OF MANUFACTURING THE SAME

BACKGROUND OF THE INVENTION

Field of the Invention

The present invention relates to a multi-point probe and an electronic contact sheet for configuring the same, a multi-point probe array, and a multi-point probe manufacturing method.

Priority is claimed on Japanese Patent Application No. 2013-107229, filed May 21, 2013, the content of which is incorporated herein by reference.

Description of Related Art

A technology of detecting biological signals generated from a biological surface and inside of a living body is paid attention to as a next-generation medical technology for realizing a healthy and affluent society, because not only is the current health condition grasped, but also a disease which may occur in the future can be detected in advance.

It is extremely important to detect the biological signal with high spatial resolution, in order to specifically investigate diseases.

For example, the detection of an electrical signal of biological tissues such as the brain or the spinal cord is performed by inserting a probe having a distal end portion where a plurality of electronic contacts for voltage detection are formed to the brain (for example, PTLs 1 and 2)

A probe disclosed in PTL 1 has a configuration in which an electronic contact and a wiring connected thereto are provided on a sheet-shaped or a plate-shaped insulating base material (hereinafter, suitably referred to as a "flat insulating base material").

In addition, a probe disclosed in PTL 2 has a configuration in which a probe electronic contact installed to stand and a wiring connected thereto are provided on a plate-shaped insulating base material, in the same manner as described above.

Meanwhile, the inventors have proposed a device which electrically, chemically, and mechanically detects biological signals by spirally winding an electronic contact which detects an electrical signal or a sheet-shaped insulating base material on which an electronic contact such as a sensor is formed, around a side surface of a tubular structure such as a catheter or an endoscope (NPL 1). In this method, a plurality of electronic contacts can be installed on a surface of a tubular structure.

In a device to be applied to a living body, a configuration of not only detecting a biological signal, but also detecting biological information with an electronic contact for applying stimulation to a living body or a combination of input and output electronic contacts for applying stimulation to a living body and detecting a response thereof is known.

CITATION LIST

Patent Literature

[PTL 1] Japanese Patent No. 4406697

[PTL 2] Japanese Unexamined Patent Application, First Publication No. 2012-130519

Non-Patent Literature

[NPL 1] Tsuyoshi Sekitani, Ute Zschieschang, Hagen Klauk, Takao Someya, "Flexible organic transistors and circuits with extreme bending stability", Nature Material 9, 1015-1022, 2010.

SUMMARY OF THE INVENTION

However, it is possible to investigate an electrical signal of a part of the brain by the probe disclosed in PTLs 1 and 2, but three-dimensional spatial resolution thereof is not sufficiently performed, and a probe in which electronic contacts are formed over an large range with extremely high density is required for investigating signal transmission between different parts of the brain.

In the sheet-shaped probe disclosed in NPL 1, when electronic contacts are formed over a large range with high density, a distance for spiral winding increases, the number of wirings significantly increases, signal detection accuracy is decreased due to an increase in resistance of the wirings, and the number of electronic contacts is limited due to the number of wirings.

The invention is made in view of such circumstances, and an object of the invention is to provide a multi-point probe which can realize significantly high spatial resolution, compared to a probe in the related art, an electronic contact sheet for configuring the same, a multi-point probe array and, a multi-point probe manufacturing method.

The invention employs the following means in order to solve the problems described above.

According to an aspect of the invention, there is provided a multi-point probe which is formed of a tubular laminate which is configured by winding an electronic contact sheet including a sheet-shaped insulating base material, a plurality of electronic contacts which are arranged to be separated from each other in a column shape on the sheet-shaped insulating base material, and a plurality of wirings which are connected to each of the electronic contacts on the sheet-shaped insulating base material from a first end towards a second end and laminating the electronic contact sheet to have multiple layers, in which the electronic contacts are not covered with the sheet-shaped insulating base material and are exposed, and the wirings other than a wiring on the uppermost layer are laminated so that at least some parts thereof are covered with the sheet-shaped insulating base material.

In this specification, the "electronic contacts" broadly means a portion through which current flows, such as, for example, an electrode.

In the multi-point probe according to the aspect of the invention, the multi-point probe includes a shaft-shaped core and the electronic contact sheet is wound around an outer peripheral surface of the core.

In the multi-point probe according to the aspect of the invention, the plurality of electronic contacts are arranged on one surface of the sheet-shaped insulating base material along an edge portion on the first end side of the electronic contact sheet.

In the multi-point probe according to the aspect of the invention, the sheet-shaped insulating base material is formed so that the edge portion recedes from the first end towards the second end of the tubular laminate.

In the multi-point probe according to the aspect of the invention, the plurality of electronic contacts are arranged spirally in an axial direction of the tubular laminate.

In the multi-point probe according to the aspect of the invention, the plurality of wirings are extended along an axis line direction of the tubular laminate over a predetermined range using the plurality of electronic contacts as a starting point.

In the multi-point probe according to the aspect of the invention, a plurality of pads which are connected to each of the wirings and connected to an external circuit are arranged in the vicinity of the second end of the electronic contact sheet along the second end.

In the multi-point probe according to the aspect of the invention, the electronic contact sheet is covered with a first insulating material so that the plurality of electronic contacts and the plurality of pads are exposed.

In the multi-point probe according to the aspect of the invention, a first shielding conductive layer is formed on a surface other than the surface of the sheet-shaped insulating base material where the wirings are arranged.

In the multi-point probe according to the aspect of the invention, a second shielding conductive layer is formed on the surface of the sheet-shaped insulating base material where the wirings are arranged.

In the multi-point probe according to the aspect of the invention, an amplifier connected to the plurality of electronic contacts is provided on the sheet-shaped insulating base material.

According to another aspect of the invention, a multi-point probe array is provided in which the plurality of multi-point probes described above are provided on a base substrate to stand apart from each other.

According to still another aspect of the invention, an electronic contact sheet configures the multi-point probe described above.

According to still another aspect of the invention, a manufacturing method of the multi-point probe described above provided in which the electronic contact sheet is wound from the first end towards the second end so that the plurality of electronic contacts are exposed, a second insulating material covers the entire electronic contact sheet, and the second insulating material on the plurality of electronic contacts, and the plurality of pads is removed.

According to the multi-point probe according to the aspect of the invention, the electronic contacts can be accumulated and disposed on the surface of the multi-point probe by employing a configuration in which the multi-point probe is formed of the tubular laminate configured by winding the electronic contact sheet from a first end towards a second end and laminating the electronic contact sheet to have multiple layers, and the electronic contacts are not covered with the sheet-shaped insulating base material and are exposed, and accordingly, arrangement of electronic contacts can be performed with high density, and the detection of an electrical signal and application of electrical stimulation can be performed with high spatial resolution. A multi-layered wiring structure is obtained by employing a configuration in which the electronic contact sheet is wound so that the wirings other than a wiring on the uppermost layer are laminated so that at least some parts thereof are covered with the sheet-shaped insulating base material, and accordingly, the wirings can be obtained with high density, and a result, the arrangement of electronic contacts can be performed with high density, compared to a probe in which the insulating base material where the electronic contacts are arranged is not wound (hereinafter, suitably referred to as a "non-wiring probe"). By increasing the number of times of winding, arrangement of electronic contacts can be performed at a significantly high density and the plurality of simultaneous signals can be detected, compared to the non-wiring probe of the related art. In the multi-point probe of the invention, it is enough to use a simple wiring layout and the wiring density may be low, compared to the arrangement of the electronic contacts at a high density of the same degree as that of the non-wiring probe of the related art.

According to the multi-point probe according to the aspect of the invention, by employing a configuration in which the multi-point probe includes a shaft-shaped core and the electronic contact sheet is wound around an outer peripheral surface of the core, the electronic contacts can be accumulated and arranged on the outer peripheral surface of the shaft-shaped core, and accordingly, arrangement of electronic contacts can be performed with high density, and the detection of an electrical signal and the application of electrical stimulation can be performed with high spatial resolution. The electronic contact sheet is wound around the core, the core is removed, and it is possible to realize a more flexible multi-point probe. In a case of using the multi-point probe in a living body by removing the core, it is possible to decrease damage applied to a living body due to vibration.

According to the multi-point probe according to the aspect of the invention, by employing a configuration in which the plurality of electronic contacts are arranged on one surface of the sheet-shaped insulating base material along an edge portion on the first end side of the electronic contact sheet, arrangement of electronic contacts can be performed with high density on the outer peripheral surface of the tubular laminate. For example, in a case of a rectangular electronic contact sheet, the electronic contacts can be arranged densely with respect to the axis line of the tubular laminate and the electronic contacts can be arranged with high density, only by winding the edge portion so as to be inclined with respect to the axis line.

According to the multi-point probe according to the aspect of the invention, by employing a configuration in which the sheet-shaped insulating base material is formed so that the edge portion recedes from the first end towards the second end of the tubular laminate, the electronic contacts can be arranged densely with respect to the axis line of the tubular laminate and the electronic contacts can be arranged with high density, only by arranging the electronic contacts along the edge portion and winding the electronic contact sheet around the core so that the edge portion is inclined with respect to the axis line of the tubular laminate.

According to the multi-point probe according to the aspect of the invention, by employing a configuration in which the plurality of electronic contacts are arranged spirally in an axial direction of the tubular laminate, the electronic contacts can be arranged densely on the outer peripheral surface of the tubular laminate and the electronic contacts can be arranged at a high density.

According to the multi-point probe according to the aspect of the invention, by employing a configuration in which the plurality of wirings are extended along an axis line direction of the tubular laminate over a predetermined range using the plurality of electronic contacts as a starting point, the number of times of laminating is decreased and it is possible to decrease crosstalk, compared to a configuration in which the wirings are arranged to be inclined with respect to the axis line direction of the tubular laminate. In addition, since the thickness of a portion where the wirings are formed is greater than a portion where the wirings are not formed, the number of times of laminating is decreased, and accordingly, a thickness of a multi-layered wiring structure is decreased. Further, the layout of the wirings is simple, and therefore, the wirings can be performed with high density.

According to the multi-point probe according to the aspect of the invention, by employing a configuration in which a plurality of pads are arranged in the vicinity of the other end of the electronic contact sheet along the other end, the plurality of pads can be arranged, and as a result, arrangement of electronic contacts can be performed with high density. That is, the other end of the electronic contact sheet is a portion remaining on the outermost surface of the probe after the winding, the end portion is not covered with the electronic contact sheet, and accordingly, it is possible to arrange electronic contacts with high density. With respect to this, the electronic contact sheet covers and is overlapped on the edge portion positioned between the first end and the second end of the electronic contact sheet, by winding, and accordingly, when the pads are formed on this edge portion, the pads can only be formed in the range of the outer periphery of the tubular laminate on the other end side. Accordingly, it is difficult to form the plurality of pads and as a result, it is difficult to arrange the electronic contacts with high density.

According to the multi-point probe according to the aspect of the invention, by employing a configuration in which the electronic contact sheet is covered with a first insulating material so that the plurality of electronic contacts and the plurality of pads are exposed, the wirings are coated with the first insulating material and insulation is ensured. By the winding of the electronic contact sheet, the surface of the wirings are covered with the other surface of the sheet-shaped insulating base material to ensure the insulation, but the wirings are further coated with the first insulating material to ensure the insulation.

According to the multi-point probe according to the aspect of the invention, by employing a configuration in which a first shielding conductive layer is formed on a surface other than the surface of the sheet-shaped insulating base material where the wirings are arranged, crosstalk between the wirings between the layers of the multi-layered wiring structure is decreased.

According to the multi-point probe according to the aspect of the invention, by employing a configuration in which a second shielding conductive layer is formed on a surface where the wirings are arranged, crosstalk between the wirings between the layers of the multi-layered wiring structure is decreased.

According to the multi-point probe according to the aspect of the invention, by employing a configuration in which an amplifier connected to the plurality of electronic contacts is provided on the sheet-shaped insulating base material, a weak signal (input voltage) can be effectively amplified.

According a manufacturing method of the multi-point probe according to the aspect of the invention, by employing a configuration in which the electronic contact sheet is wound from the first end towards the second end so that the plurality of electronic contacts are exposed, a second insulating material covers the entire electronic contact sheet, and the second insulating material on the plurality of electronic contacts, and the plurality of pads is removed, it is possible to manufacture a multi-point probe which is reliably insulated.

BRIEF DESCRIPTION OF THE DRAWINGS

FIG. 5 shows a composition or a conductive material which can be used in an electronic contact material of the multi-point probe of the invention, in which

FIG. 6 shows high-resolution cross-sectional transmission electron microscope images (TEM images), in which

DETAILED DESCRIPTION OF THE INVENTION

Hereinafter, configurations of a multi-point probe to which the invention is applied and an electronic contact sheet for configuring the same, a multi-point probe array, and a multi-point probe manufacturing method will be described with reference to the drawings. The drawings used in the following description show enlarged parts of characteristics for convenience to make the characteristics clearly understandable, in some cases, and the ratio of dimensions or the like of each constituent element is not the same as those of the actual invention. Materials, dimensions, and the like exemplified in the following invention are merely exemplary examples, the invention is not limited thereto, and it is possible to perform suitable modifications within a range not departing from the gist thereof. A multi-point probe, an electronic contact sheet, and a multi-point probe array of the invention may include a constituent element such as a layer not disclosed below, in a range to obtain the effects of the invention.

(Multi-Point Probe)

Figure 1:
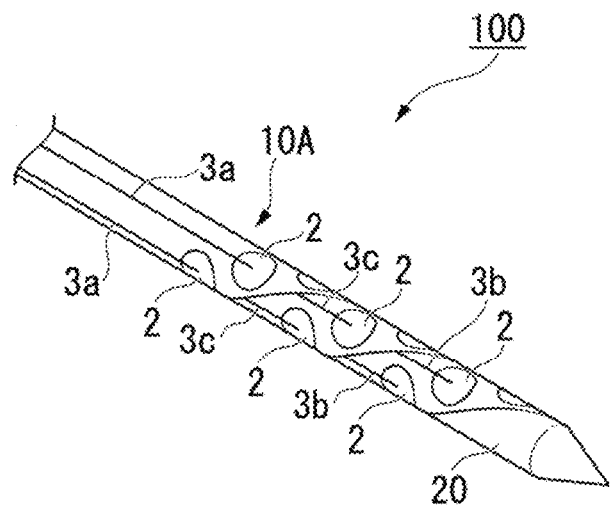
FIG. 1 is a perspective view showing an example of a multi-point probe according to one embodiment of the invention.
Figure 2:
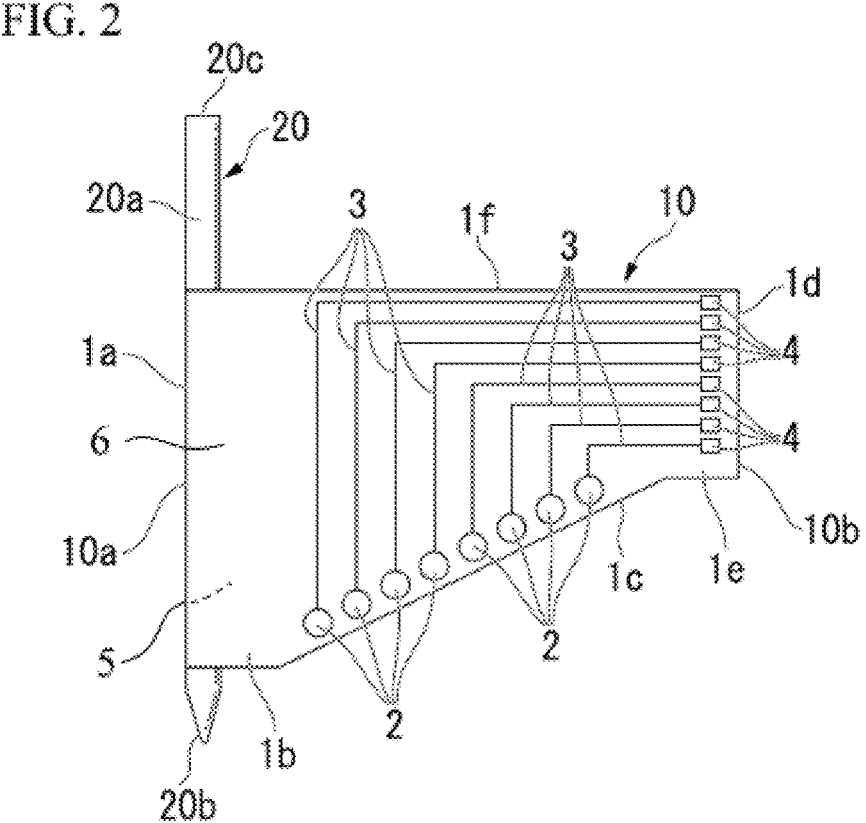
FIG. 2 is a schematic view showing a state where a wound electronic contact sheet of the multi-point probe shown in FIG. 1 is unwound for the description.

FIG. 1 is a perspective view showing an example of a multi-point probe according to one embodiment of the invention. FIG. 2 is a schematic view showing a state where a wound electronic contact sheet of the multi-point probe shown in FIG. 1 is unwound for the description. FIG. 1 and FIG. 2 show a multi-point probe having a configuration including a core.

In the description of the multi-point probe, an electronic contact sheet according to one embodiment of the invention will be also described.

A multi-point probe 100 is a multi-point probe which is formed of a tubular laminate 10A which is configured by winding an electronic contact sheet 10 from its first end (one end) 10a towards its second end 10b (the other end) and laminating the electronic contact sheet to have multiple layers. The electronic contact sheet 10 includes a sheet-shaped insulating base material, and a plurality of electronic contacts 2 which are arranged to be separated from each other, a plurality of wirings 3 (3a, 3b, and 3c) which are connected to electronic contacts 2, and a plurality of pads 4 which are connected to the wirings 3 and an external circuit (not shown) on the sheet-shaped insulating base material 1. The electronic contacts 2 are not covered with the sheet-shaped insulating base material 1 and exposed, and the wirings 3 other than a wiring 3a on the uppermost layer (that is, wirings shown with reference numerals 3b and 3c in FIG. 1) are laminated so that some parts thereof are covered with the sheet-shaped insulating base material. In the multi-point probe shown in FIG. 1, the plurality of pads are provided, but the pads are not compulsory constituent elements for the multi-point probe of the invention.

The multi-point probe 100 shown in FIG. 1 and FIG. 2 further includes a shaft-shaped core 20 and the electronic contacts 2 are wound around an outer peripheral surface 20a of the core 20, but the shaft-shaped core 20 may not be included. The shaft-shaped core may be detachably included in the multi-point probe, and the multi-point probe may be used by removing the core at a suitable timing, for example, after being mounted. When the multi-point probe does not include the core, it is possible to realize a more flexible multi-point probe. In a case of using the multi-point probe in a living body by removing the core, it is possible to decrease damage applied to a living body due to vibration.

In the multi-point probe shown in FIG. 1, a rod-shaped material is shown as the shaft-shaped core, but if the sheet-shaped insulating base material can be wound around the core, the shape thereof is not limited to the rod shape and a flexible material may be used. In addition, hardness thereof may change depending on conditions such as a temperature.

Figure 14A:
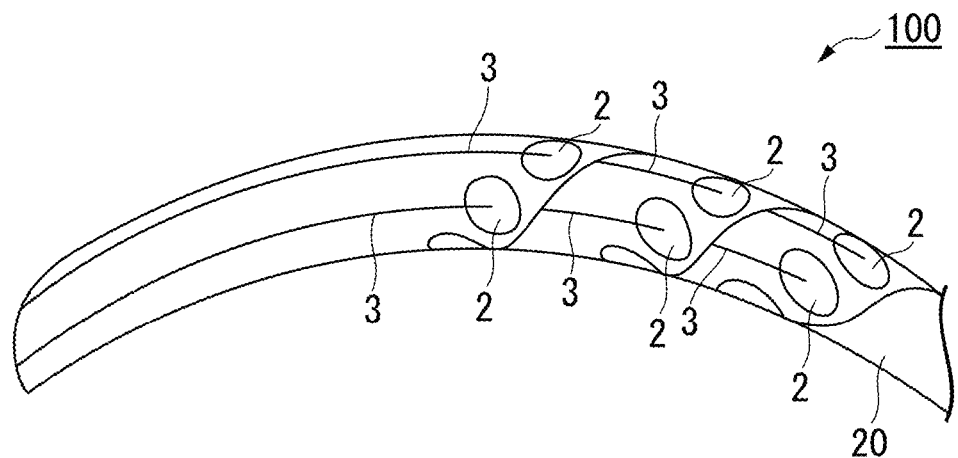
FIG. 14 is a perspective view showing an example of the multi-point probe according to another embodiment of the invention.
Figure 14B:
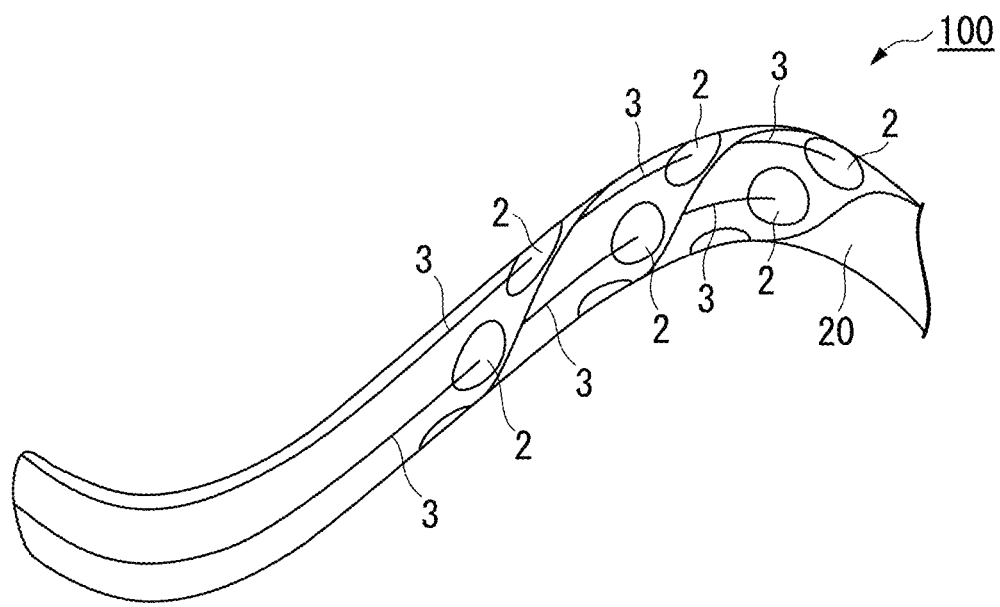

FIG. 14A and FIG. 14B show a part of an example of a multi-point probe using a flexible shaft-shaped core. As an application example of such a multi-point probe, a catheter or an endoscope is used.

The electronic contact sheet 10 includes the plurality of electronic contacts 2, the plurality of wirings 3, and the plurality of pads 4 on one surface 1a of the sheet-shaped insulating base material 1.

Since the electronic contact sheet 10 including the wirings 3 is wound around one surface 1a of the insulating base material 1, the multi-point probe 100 has a wiring structure in which layers (sheets) including wirings formed thereon are laminated. It was extremely complicated to produce such a multi-wiring structure by a method of the related art, but in the multi-point probe of the invention, the multi-wiring structure is formed only by winding. As the number of times the layers (sheets) are wound including the wirings formed thereon increases, it is possible to increase the number of total wirings, and as a result, it is possible to increase the number of electronic contacts which can be arranged. By arranging the plurality of electronic contacts on the surface, arrangement of electronic contacts can be performed with high density, and accordingly, the detection of an electrical signal and application of electrical stimulation can be performed with high spatial resolution.

The sheet-shaped insulating base material 1 is formed of an insulating material having flexibility so as to be wound around, and specific examples thereof include polymer materials such as polyimide, polyethylene terephthalate, polyethylene naphthalate, polyether ether ketone, and para-xylylene. By using an elastomer such as silicon rubber in the insulating base material 1, it is possible to realize a flexible multi-point probe with a combination with the flexible core.

A thickness thereof is not limited, but can be from 1 μm to 20 μm, for example. For example, when a sheet-shaped insulating base material having a thickness of 1 μm is used, the thickness of the laminated multi-layered sheet is approximately 30 μm, even when the sheet is wounded 30 times.

The shape of the sheet-shaped insulating base material 1 is not particularly limited, but it is necessary that the sheet-shaped insulating base material (that is, electronic contact sheet) is wound so that the plurality of electronic contacts 2 are exposed.

For example, in a case where the plurality of electronic contacts are arranged along a side end, of a rectangular sheet-shaped insulating base material, between the first end and the other end to be wound, the sheet is wound so as to be inclined with respect to an axis line of the tubular laminate 10A (in a case of the configuration shown in the drawing, to coincide with an axis line of the core 20), so that the plurality of electronic contacts are exposed.

In the example shown in FIG. 1 and FIG. 2, the sheet-shaped insulating base material 1 has a shape in which a first rectangular portion 1b is provided in a predetermined range from one end (starting end) which starts to be wound around the core 20, an edge portion 1c on one end 20b side of the core 20 is formed so as to recede towards the other end 20c from one end 20b of the core 20, and a second rectangular portion (vicinity of the other end) 1e where the pads 4 are arranged, is provided on an end (the other end) 1d on a side opposite to the starting end. An edge portion if on the side opposing the edge portion 1c is formed without receding from the edge portion of the first rectangular portion 1b.

In the example shown in FIG. 1 and FIG. 2, the plurality of electronic contacts 2 are arranged along the edge portion 1c and the plurality of pads 4 are arranged in the second rectangular portion (vicinity of the other end) 1e along the other end 1d.

As shown in the example shown in FIG. 1 and FIG. 2, the sheet-shaped insulating base material 1 has a region in which the edge portion 1c on the one end 20b side of the core 20 is formed so as to recede from the one end 20b towards the other end 20c of the core 20 and the electronic contact sheet 10 having a configuration in which the plurality of electronic contacts 2 are arranged along the edge portion 1c, and accordingly, the plurality of electronic contacts 2 are exposed only by performing winding with respect to the axis line of the core 20 without particularly inclining. As illustrating in FIG. 2, first shielding conductive layer 5 is formed on the bottom surface of the insulting base material, Second shielding conductive layer 6 is formed on the upper surface of the insulting base material.

The electronic contacts 2 are set as an interface which comes into contact with a target and detects an electrical signal, for example, according to the purpose of the multi-point probe and applies the electric stimulation.

The electronic contacts 2 are arranged to be separated from each other on the surface 1a of the sheet-shaped insulating base material 1 on a side opposite to the surface wound on the core 20, and the number thereof is not particularly limited, and the plurality of electronic contacts can be arranged by using a core having a large area of an outer peripheral surface.

The electronic contacts 2 are preferably arranged at intervals of 10 µm to 200 µm and a diameter of each electronic contact 2 is preferably from 5 µm to 100 µm. The shape thereof is not particularly limited, and can be a circular shape or a square shape, for example.

Figure 3:
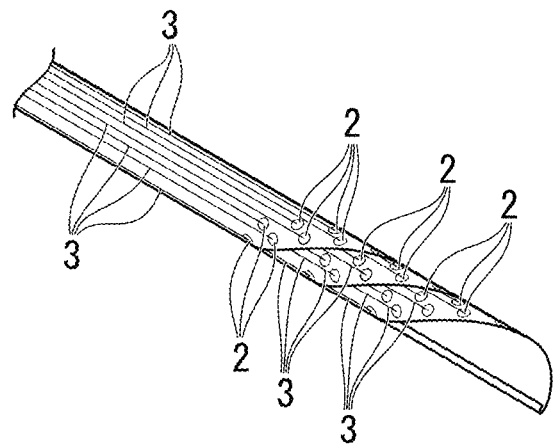
FIG. 3 is a schematic view for showing another arrangement of electronic contacts of a multi-point probe of the invention.

The arrangement of the electronic contacts 2 is not particularly limited, and for example, the electronic contacts may be arranged along the edge portion 1c on the first end side of the electronic contact sheet 10, and as shown in FIG. 1, the electronic contacts are spirally arranged based on the axis line of the tubular laminate 10A (in a case of the configuration shown in the drawing, to coincide with an axis line of the core 20). In addition, as shown in FIG. 3, the electronic contacts may be arranged in two columns or three or more columns along the edge portion with a level difference.

As the material of the electronic contacts 2, a metal material which is hardly corroded such as gold or platinum is preferably used.

A flexible nanomaterial such as carbon nanotubes (CNT) may be used as the material of the electronic contacts 2.

For example, the carbon nanomaterial doubly covered with molecules constituting hydrophilic ionic liquid and a water-soluble polymer are dispersed in a water-soluble polymer medium, and a gel conductive material (conductive gel) obtained by crosslinking the water-soluble polymer may be used. The conductive gel will be described below.

The wirings 3 connect the corresponding electronic contacts 2 and the pads 4, and the wirings are arrange apart from each other on the surface 1a of the sheet-shaped insulating base material 1 on a side opposite to the surface to be wound around the core 20, in the same manner as a case of the electronic contacts 2.

The wirings 3 are preferably arranged at intervals of 5 µm to 200 µm and the width thereof is preferably from 2 µm to 100 µm.

As the material of the wirings 3, a metal material which is hardly corroded such as gold or platinum is preferably used.

The plurality of wirings 3 can be arranged by using the sheet-shaped insulating base material 1 having a large width (length in a winding direction). The wirings can be laminated on the outer peripheral surface of the core by winding, even when the sheet-shaped insulating base material 1 having an extremely large width is used and the number of wirings is increased, and accordingly, it is not necessary to increase the size of the entire multi-point probe.

In the example shown in FIG. 1 and FIG. 2, the wirings 3 are extended along an axis line direction of the core 20 over a predetermined range using the electronic contacts 2 as a starting point. That is, the wirings 3 are extended to the edge portion if side along the axis line direction of the core 20 using the electronic contacts 2 as a starting point. At the edge thereof, the wirings 3 are extended to the pad 4 arranged on the second rectangular portion 1d by changing an angle.

In the configuration in which the wirings 3 are extended along the axis line direction of the core 20, a length of the wirings is decreased, the number of times of laminating is decreased, and it is possible to decrease crosstalk, compared to a configuration in which the wirings are arranged to be inclined to the axis line direction of the core.

The pads 4 are connected to the corresponding wirings 3 and connected to an external circuit such as a measurement device or a voltage application device for an electrical signal according to the purpose of the multi-point probe, and the pads are arrange apart from each other on the surface 1a of the sheet-shaped insulating base material 1 on a side opposite to the surface to be wound around the core 20, in the same manner as a case of the electronic contacts 2 and the wirings 3.

The pads 4 are preferably arranged at intervals of 50 µm to 1000 µm and the width of the pads 4 is preferably from 20 µm to 500 µm.

The shape thereof is not particularly limited, and can be a circular shape or a square shape, for example. The mounting can be easily performed by arranging the pads in plural stages in a zigzag manner.

As shown in FIG. 2, the pads 4 may be arranged in the vicinity (position of the second rectangular portion 1e) of the second end 10b of the electronic contact sheet 10 along the second end 10b. In the configuration, since the second end 10b of the electronic contact sheet 10 is a portion remaining on the outermost surface of the probe after the winding, the end portion is not covered with the electronic contact sheet, and accordingly, it is possible to arrange electronic contacts with high density and as a result, it is possible to arrange the plurality of electronic contacts. With respect to this, in a configuration in which the pads are arranged along the edge portion if of the sheet-shaped insulating base material 1 positioned between the first end 10a and the second end 10b of the electronic contact sheet 10, the electronic contact sheet covers and is overlapped on the edge portion if by winding, and accordingly, the pads can only be arranged in a region corresponding to the length of the outer periphery of the rod of the core 10. Therefore, it is difficult to form the plurality of pads, and as a result, it is difficult to arrange the electronic contacts with high density.

As the material of the pads 4, a metal material which is hardly corroded such as gold or platinum is preferably used.

A flexible nanomaterial such as carbon nanotubes (CNT) or the gel conductive material (conductive gel) may be used as the material of pads 4, in the same manner as that of the electronic contacts 2.

The core 20 has a shaft shape and the shape thereof is not limited as long as the electronic contact sheet can be wound and fixed, but a columnar shape is preferably used, from a viewpoint of ease of winding and fixing. As shown in FIG. 1 and FIG. 2, a distal end portion to be inserted into a target of the detection of the electrical signal or the application of electrical stimulation, preferably has a tapered shape, from a viewpoint of ease of insertion.

The diameter and the length of the core 20 are not particularly limited, and can be selected according to the purpose.

The material of the core 20 is not limited, and for example, metal having rigidity such as stainless steel, tungsten, or titanium, engineering plastics such as polyacetal, or a resin having flexibility such as silicon rubber, polypropylene, polyethylene, or polyethylene terephthalate can be used.

In the electronic contact sheet 10, a first insulating material (not shown) may be coated on the one surface 1a of the sheet-shaped insulating base material 1 so that the plurality of electronic contacts 2 and the plurality of pads 4 are exposed.

The material of the first insulating material is not limited and Parylene (registered trademark) and Cytop (registered trademark) can be used, for example. Parylene can be coated by a CVD method and Cytop can be coated by dipping, for example.

A thickness of the coated layer of the first insulating material is preferably from 1 μm to 10 μm.

In the electronic contact sheet 10, a first shielding conductive layer (not shown) may be formed on a surface on a rear side of the one surface 1a of the sheet-shaped insulating base material 1. In the configuration, crosstalk between the wirings between the layers of the multi-layered wiring structure is decreased.

The material of the first shielding conductive layer is not limited, and gold can be used, for example.

A thickness of the first shielding conductive layer is preferably from 0.02 μm to 0.2 μm.

Figure 4:
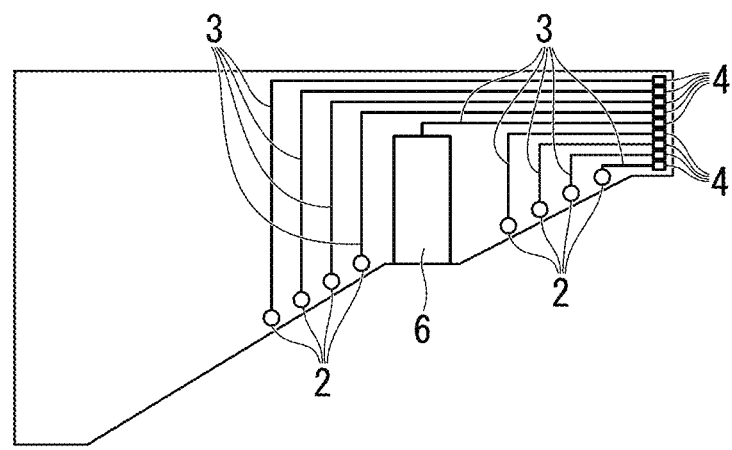
FIG. 4 is a perspective view showing an example of a multi-point probe according to another embodiment of the invention.

As shown in FIG. 4, in the electronic contact sheet 10, a second shielding conductive layer 6 may be formed on the one surface 1a of the sheet-shaped insulating base material 1. In this configuration, crosstalk between the wirings between the layers of the multi-layered wiring structure is decreased.

The material of the second shielding conductive layer is not limited, and gold can be used, for example.

A thickness of the second shielding conductive layer is preferably from 0.02 μm to 0.2 μm. The second conductive layer can be formed at the same time with the wirings.

Both of the first shielding conductive layer and the second shielding conductive layer may be provided.

The electronic contact sheet 10 may include an amplifier connected to the plurality of electronic contacts 2 on the one surface 1a of the sheet-shaped insulating base material 1.

When winding the electronic contact sheet 10 around the outer peripheral surface 20a of the core 20, the first end 10a of the electronic contact sheet 10 is fixed to and started to be wound around the outer peripheral surface 20a of the core 20 using an epoxy adhesive or an acrylate adhesive, and then, a front surface and a rear surface of the electronic contact sheet 10 are mounted using an adhesive by winding once and continuing to be wound, and a rear surface of the second end 10b of the electronic contact sheet 10 is finally adhered to the front surface of the electronic contact sheet 10 using an adhesive, and the winding is completed.

In the multi-point probe of the invention, after winding the electronic contact sheet 10 around the outer peripheral surface 20a of the core 20, the second insulating material covers the entire electronic contact sheet, and then the second insulating material on the plurality of electronic contacts and the plurality of pads is removed to expose the electronic contacts and the pads.

The material of the second insulating material is not limited and Parylene (registered trademark) and Cytop (registered trademark) can be used, for example.

By employing a configuration of coating the entire electronic contact sheet with the second insulating material, a difference in level of the wound electronic contact sheet is covered, and accordingly, the multi-point probe is easily inserted into a target.

As a method of removing the second insulating material on the plurality of electronic contacts and the plurality of pads, a method using a laser is used, for example.

The multi-point probe of the invention can be used for detection of an electrical signal of biological tissues such as the brain or the spinal cord or application of electrical stimulation to biological tissues, but the multi-point probe can also be used for the purpose of signal transmission and reception of a nerve cell or a muscle cell or measurement of concentration of calcium ion or glucose. The applied target is not limited to a living body. For example, a sensor such as an ultrasonic sensor or an optical sensor, or an element such as a light receiving element or an ultrasonic element can be used. By embedding the sensor on a surface of a catheter or an endoscope, it is possible to enlarge the application range of inspection or treatment.

(Gel Conductive Material (Conductive Gel))

As described above, as the material of the electronic contacts configuring the multi-point probe of the invention, the electronic contacts, and the multi-point probe array, the carbon nanomaterial doubly covered with molecules constituting hydrophilic ionic liquid and a water-soluble polymer are dispersed in a water-soluble polymer medium, and a gel conductive material (conductive gel) obtained by crosslinking the water-soluble polymer may be used.

In this specification, the ionic liquid is also referred to as an ordinary temperature molten salt or simply as a molten salt and is defined as a salt which is in a molten state in a wide temperature range including ordinary temperature.

Among various hydrophilic ionic liquids which are known in the related art, a hydrophilic ionic liquid can be used, and examples thereof include N,N-diethyl-N-methyl-N-(2-methoxyethyl)ammonium tetrafluoroborate (DEMEBF$_4$).

In this specification, the carbon nanomaterial refers to a material in which a constituent element (for example, one CNT) having a nanometer-size structure is formed of carbon atoms, and the carbon atoms of the constituent element are bonded to each other with the Van der Waals force. Examples of the carbon nanomaterial includes carbon nanotubes, carbon nanofibers (carbon fibers having a diameter of 10 nm or less), carbon nanohorns, and fullerenes. When a fine carbon nanomaterial having a diameter of 10 nm or less is used, superior dispersibility is exhibited in water.

The same type of carbon nanomaterial may be used, or different types of carbon nanomaterials may be used.

Carbon nanotubes have a structure in which a single-layer or multi-layer graphene sheet with hexagonally arranged carbon atoms is rolled up in a cylindrical shape (referred to as single-wall nanotubes (SWNTs), double-wall nanotubes (DWNTs), or multi-wall nanotubes (MWNTs)). The carbon nanotubes which can be used as the carbon nanomaterial are not particularly limited and may be any one of SWNTs, DWNTs, and MWNTs. In addition, generally, carbon nanotubes can be manufactured by using, for example, a laser ablation method, arc discharge, a thermal CVD method, a plasma CVD method, a gas-phase method, or a combustion method. In addition, plural types of carbon nanotubes may be used.

The carbon nanotubes are likely to aggregate due to the Van der Waals force between the carbon nanotubes and are present in a state that plural carbon nanotubes form a bundle or an aggregate. However, the bundle or the aggregate can be pulverized (the degree of entanglement among the carbon nanotubes can be decreased) by applying a shearing force thereto in the presence of the ionic liquid. By sufficiently pulverizing the bundle or the aggregate, the Van der Waals force, which causes the carbon nanotubes to aggregate, is weakened, the carbon nanotubes can be separated into individual carbon nanotubes, and the ionic liquid can be adsorbed onto the individual carbon nanotubes. As a result, a composition consisting of an ionic liquid and carbon nanotubes, which includes a single carbon nanotube covered with the molecules constituting the ionic liquid, can be obtained.

The means for applying a shearing force which is used in the pulverizing step is not particularly limited, and a wet pulverizer which can apply a shearing force, for example, a ball mill, a roller mill, or a vibrating mill can be used.

The carbon nanotubes and the ionic liquid are mixed with each other, and then the pulverizing step is performed. As a result, it is thought that the gel composition is formed because the molecules constituting the ionic liquid, which is bonded to the surfaces of the less entangled carbon nanotubes through the "cation-π" interaction, serve to combine the carbon nanotubes with one another through ionic bonding (PTL 2). As described below, by rinsing this gel composition by using, for example, saline solution or ethanol, a single layer of the molecules constituting the ionic liquid can be formed on the surfaces of the carbon nanotubes. Further by mixing water and the water-soluble polymer with the carbon nanotubes covered with the molecules constituting the ionic liquid, a composition can be manufactured in which the carbon nanotubes covered with the molecules constituting the ionic liquid are dispersed in a water-soluble polymer medium.

In this specification, the water-soluble polymer (medium) is not particularly limited as long as it is a polymer which can be dissolved or dispersed in water, and it is more preferable that the water-soluble polymer can be crosslinked in water. For example, the following examples can be used.

1. Synthetic Polymer
(1) Ionic
  Polyacrylic acid (anionic)
  Polystyrene sulfonic acid (anionic)
  Polyethyleneimine (cationic)
  MPC polymer (amphoteric)

(2) Nonionic
  Polyvinylpyrrolidone (PVP)
  Polyvinyl alcohol (saponified polyvinyl acetate)
  Polyacrylamide (PAM)
  Polyethylene oxide (PEO)
2. Natural Polymer (Mostly Polysaccharides)
  Starch
  Gelatin
  Hyaluronic acid
  Alginic acid
  Dextran
  Protein (for example, water-soluble collagen)
3. Semi-synthetic Polymer (For Example, Solubilized Cellulose)
  Cellulose derivatives such as carboxymethyl cellulose (CMC), hydroxypropyl cellulose (HPC), or methyl cellulose (MC)
  Water-soluble chitosan (which may also be classified into "2. Natural Polymer")

In addition, specific examples of the water-soluble polymer include polyrotaxane. Polyrotaxane is obtained by disposing a blocking group at both terminals of pseudo-polyrotaxane (both terminals of a linear molecule) so as to prevent a cyclic molecule from leaving, the pseudo-polyrotaxane having a structure in which the linear molecule (axis) is included in a cavity of the cyclic molecule (rotator) in a state of being skewered. For example, polyrotaxane containing α-cyclodextrin as the cyclic molecule and polyethylene glycol as the linear molecule can be used.

In addition, as the water-soluble polymer medium, a compound having a group, which is reactive with a cross-linking agent, is more preferably because it forms a firm film by crosslinking.

In order to form a fine-shaped pattern by using the composition or the conductive material, it is preferable that the water-soluble polymer be photo-crosslinkable polymer.

The layer of the molecules constituting the ionic liquid which cover the carbon nanomaterial may be a monomolecular layer. The molecules constituting the ionic liquid are bonded to the surface of the carbon nanomaterial through the "cation-π" interaction. Therefore, the layer of the molecules constituting the ionic liquid which cover the carbon nanomaterial can be made to be a monomolecular layer by selecting a combination of the carbon nanomaterial and the ionic liquid in which a bonding strength between the molecules constituting the ionic liquid is lower than a bonding strength which is obtained through the "cation-π" interaction.

For example, the layer of molecules of N,N-diethyl-N-methyl-N-(2-methoxyethyl)ammonium tetrafluoroborate ($DEMEBF_4$) which cover the carbon nanomaterial can be made to be a monomolecular layer by selecting carbon nanotubes as the carbon nanomaterial and selecting $DEMEBF_4$ as the ionic liquid. Further, for example, when polyrotaxane is selected as the water-soluble polymer, a thin layer of polyrotaxane having a thickness of about 5 nm can be formed on the monomolecular layer of $DEMEBF_4$. In a composition obtained as above, the dispersion concentration of the carbon nanotubes can be made to be high, and a material having high conductivity can be obtained. In a conductive member such as an electrode which is manufactured by using the conductive material, electrons migrate between the carbon nanotubes through the thin $DEMEBF_4$ molecular layer and the thin polyrotaxane layer.

In the conductive material, the molecules constituting the ionic liquid are strongly bonded to the surface of the carbon nanomaterial through the "cation-π" interaction. Therefore, the molecules constituting the ionic liquid which are bonded to the surface of the carbon nanomaterial are not released outside the water-soluble polymer medium. The molecules constituting the ionic liquid which are not bonded to the surface of the carbon nanomaterial are removed by rinsing by using, for example, saline solution or ethanol.

In the conductive material, the carbon nanomaterial included therein is doubly covered with the molecules constituting the ionic liquid molecules and the water-soluble polymer. Therefore, even when the composition or the conductive material according to the present invention is used in the living body, the carbon nanomaterial does not substantially come into contact with cells in the living body. In addition, due to high flexibility, the followability to the surface of an organ or the like in the living body is superior, and a far superior interface can be formed with an organ or the like. Further, high conductivity can be obtained.

The conductive material is provided by using the method which includes a first step of mixing a hydrophilic ionic liquid, a carbon nanomaterial, and water with each other to prepare a first dispersion system in which the carbon nanomaterial covered with the molecules constituting the ionic liquid is dispersed; and a second step of mixing the first dispersion system, a water-soluble polymer, and water with each other to prepare a second dispersion system in which the carbon nanomaterial covered with the molecules constituting the ionic liquid and the water-soluble polymer are dispersed.

In the first step, the carbon nanomaterial may be pulverized by applying a shearing force to the carbon nanomaterial.

As a result, the carbon nanomaterial can be covered with the hydrophilic ionic liquid in a state that a bundle or an aggregate of the carbon nanomaterial is further separated.

The method of manufacturing a conductive material may further include, after the second step, a step of preparing a composition by crosslinking the water-soluble polymer and dispersing the carbon nanomaterial in the water-soluble polymer medium. As a result, moldability and processability can be improved.

The method of manufacturing a conductive material may further include a rinsing step of removing the molecules constituting the ionic liquid which are not bonded to the carbon nanomaterial. As a result, moldability and processability can be improved.

This rinsing step can be performed by using, for example, saline solution, ethanol, or liquid which does not destroy gel. This rinsing step may be performed at any time.

The conductive material may further include other materials within a range not impairing the effects of the present invention. The method of manufacturing the conductive material invention may further include other steps within a range not impairing the effects of the present invention.

Hereinafter, the conductive material will be described in detail based on examples. However, these examples are described to help easy understanding of the present invention, and the present invention is not limited to these examples.

EXAMPLES

Figure 5A:
FIG. 5A is an image showing a composition obtained by dispersing carbon nanotubes covered with molecules constituting $DEMEBF_4$, in polyrotaxane.

FIG. 5A is an image showing a composition before being cured with ultraviolet (UV) rays, the composition being obtained by dispersing carbon nanotubes, which is covered with molecules constituting N,N-diethyl-N-methyl-N-(2-methoxyethyl)ammonium tetrafluoroborate ($DEMEBF_4$), in polyrotaxane. It can be seen that the obtained composition was gel (in this specification, "gel" refers to a state in which there is no fluidity or substantially no fluidity relative to liquid having fluidity).

In order to prepare this composition, 30 mg of commercially available carbon nanotubes (MWNTs, length: 10 μm, diameter: 5 nm) and 60 mg of N,N-diethyl-N-methyl-N-(2-methoxyethyl)ammonium tetrafluoroborate ($DEMEBF_4$) as a hydrophilic ionic liquid were mixed with each other and were stirred in deionized water at 25° C. for 1 week by using a magnetic stirrer at a rotating speed of 700 rpm or higher. The obtained suspension was processed with a high-pressure jet-milling homogenizer (60 MPa; Nano-jet Pal, JN10, Jokoh) to obtain a black material. A solution including the obtained CNT gel was rinsed with saline solution, and then 1 mg of a photo-crosslinking agent (Irgacure 2959, manufactured by Nagase & Co., Ltd.) and 1000 mg of polyrotaxane gel ("photo-crosslinkable gel", manufactured by Advanced Softmaterials Inc.) were mixed with the solution to prepare the above-described composition.

Figure 5B:
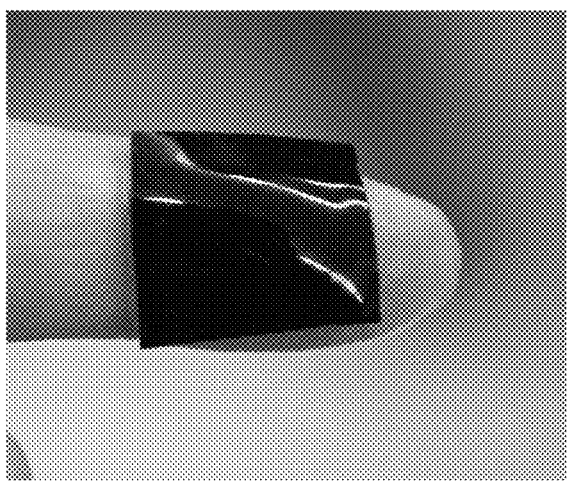
FIG. 5B is an image of a sheet obtained by performing photo-crosslinking of the composition shown in FIG. 5A.

FIG. 5B is an image showing a sheet obtained by irradiating the composition shown in FIG. 5A with ultraviolet rays (wavelength: 365 nm) for 5 minutes to be cured.

The Young's modulus of the obtained sheet was lower than 10 kPa. The Young's modulus of silicon is about 100 GPa, and the Young's modulus of a plastic film of the related art is 1 GPa to 5 GPa. Therefore, it can be seen that the sheet was extremely flexible. In addition, the Young's modulus of a brain is 1 kPa to 2 kPa, and the Young's modulus of muscle cells of a heart is 100 kPa or less. Therefore, it can be seen that the composition or the conductive material according to the embodiment of the present invention has high flexibility equal to or higher than that of an organ. Therefore, the followability to the surface of an organ is high, and a far superior interface can be formed with an organ.

Figure 5C:
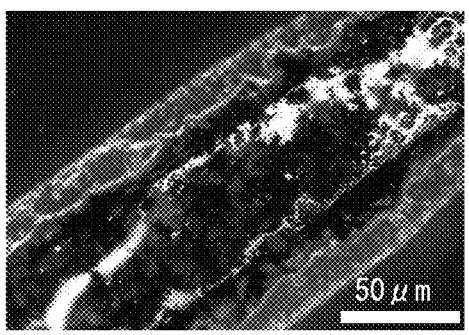
FIG. 5C is an optical microscope image showing a state after photo-crosslinking the composition shown in FIG. 5A and patterning a fine structure having a line width of about 50 μm.

FIG. 5C is an optical microscope image showing a state after photo-crosslinking the composition by using a ultrafine digital UV exposure system ("digital exposure device" manufactured by PMT Corporation) and patterning a fine structure having a line width of about 50 μm. The composition or the conductive material according to the embodiment of the present invention is a material with which fine processing can be performed.

By changing the type of the photo-crosslinkable material, crosslinking can be performed at various wavelengths. Therefore, the means of crosslinking is not limited to UV.

Figure 6A:
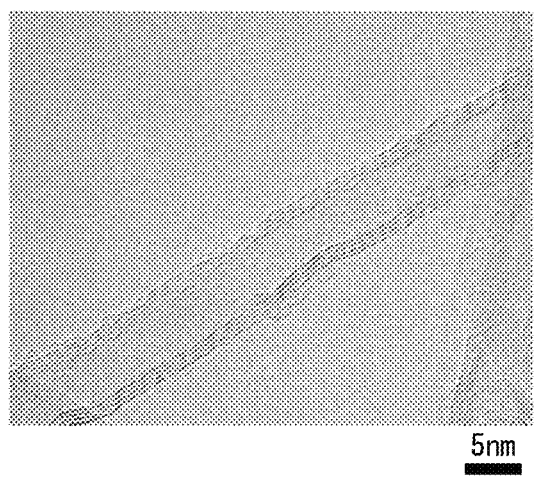
FIG. 6A is a TEM image showing a carbon nanotube which can be used in an electronic contact material of the multi-point probe of the invention.
Figure 6B:
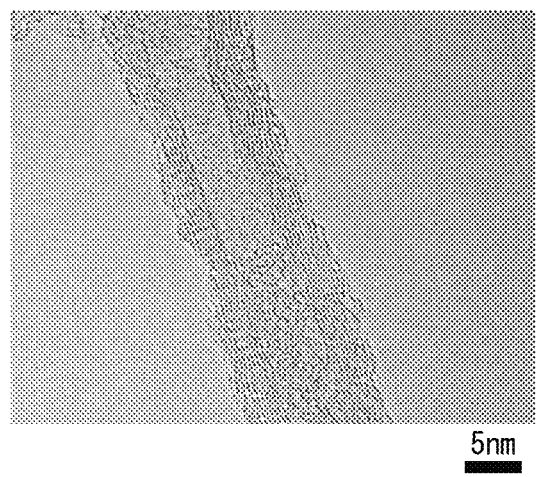
FIG. 6B is a TEM image showing a carbon nanotube covered with polyrotaxane, the carbon nanotube being obtained by mixing a carbon nanotube and polyrotaxane with each other in water without an ionic liquid and stirring the mixture while pulverizing the mixture with a jet mill.
Figure 6C:
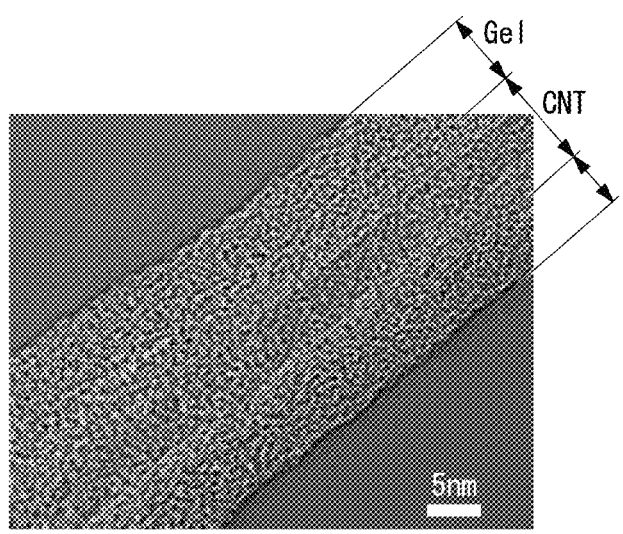
FIG. 6C is a TEM image showing a carbon nanomaterial or a composition obtained under the same conditions as the production conditions of the composition shown in FIG. 6A.

FIG. 6 is high-resolution cross-sectional transmission electron microscope images (TEM images), in which FIG. 6A is a TEM image showing a carbon nanotube (MWNT, length: 10 μm, diameter: 5 nm) which can be used in the present invention; FIG. 6B is a TEM image showing a carbon nanotube covered with polyrotaxane, the carbon nanotube being obtained by mixing 30 mg of a carbon nanotube (MWNT, length: 10 μm, diameter: 5 nm) and 100 mg of polyrotaxane ("photo-crosslinkable gel", manufactured by Advanced Softmaterials Inc.) with each other in water without an ionic liquid and stirring the mixture while pulverizing the mixture with a jet mill; and FIG. 6C is a TEM image showing a composition obtained under the same conditions as the production conditions of the composition shown in FIG. 1(a).

As a high-resolution cross-sectional transmission electron microscope, HF-2000 Cold-FE TEM (80 kV, manufactured by Hitachi High-Technologies Corporation) was used.

As shown in FIG. 6A, it can be seen that the used carbon nanotube consisted of three layers or four layers.

As shown in FIG. 6B, it can be seen that the single carbon nanotube was covered with polyrotaxane, but the thickness of the coating layer thereof was not uniform.

On the other hand, as shown in FIG. 6C, it can be seen that the thickness of the polyrotaxane layer covering the single carbon nanotube was extremely uniform and was clearly different from that of FIG. 6B.

The difference in uniformity between the thicknesses of the coating layers shows that the carbon nanotube shown in FIG. 6C was obtained by covering the layer of the molecules of the hydrophilic ionic liquid $DEMEBF_4$, which had covered the carbon nanotube, with polyrotaxane, not by covering the carbon nanotube with polyrotaxane after removing the molecules of the hydrophilic ionic liquid $DEMEBF_4$, which had covered the carbon nanotube, from the carbon nanotube. If the carbon nanotube shown in FIG. 2C was obtained by covering the carbon nanotube with polyrotaxane after removing the molecules of the hydrophilic ionic liquid $DEMEBF_4$, which had covered the carbon nanotube, from the carbon nanotube, the thickness of the coating layer shown in FIG. 6C would be nonuniform as in the case of FIG. 6B. In addition, It is considered that, since the molecules of $DEMEBF_4$ were bonded to the carbon nanotube through cation-πinteraction having a strong force comparable to the force of hydrogen bonding, the molecules of the hydrophilic ionic liquid $DEMEBF_4$ covering the carbon nanotube were not removed from the carbon nanotube.

As shown in FIG. 6, with the method of manufacturing a conductive material, a surface of a carbon nanotube can be uniformly covered with a biocompatible material with molecules constituting the ionic liquid interposed therebetween.

Figure 7:
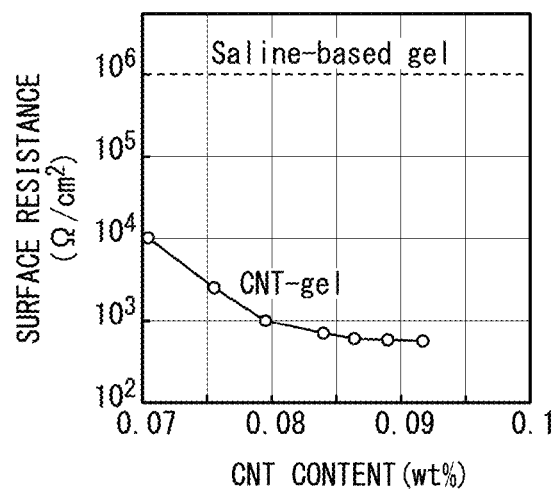
FIG. 7 is a graph showing the surface resistance of a composition (or a conductive material) which can be used in the electronic contact material of the multi-point probe of the invention and the carbon nanotube content dependency thereof

FIG. 7 is a graph showing the surface resistance of the composition (CNT-gel) and the carbon nanotube content dependency of the surface resistance. For comparison, the surface resistance of a gel (Saline-based gel) of the related art containing saline solution as a main component is also indicated by a dotted line.

The composition (CNT-gel) was obtained under the same conditions as the production conditions of the composition shown in FIG. 5A. The size of it was 1 cm×1 cm, and the thickness of it was 1 mm.

The gel (Saline-based gel) containing saline solution as a main component was obtained by adding 1 mg of a photo-crosslinking agent to 300 mg of rotaxane gel, dissolving the mixture in 100 ml of saline solution, and then photocrosslinking the solution by using UV rays. The size of it was 1 cm×1 cm, and the thickness of it was 1 mm.

As shown in FIG. 7, it can be seen that the surface resistance of the composition according to the embodiment of the present invention is lower by more than two or three digits than that of the gel of the related art containing saline solution as a main component.

Figure 8:
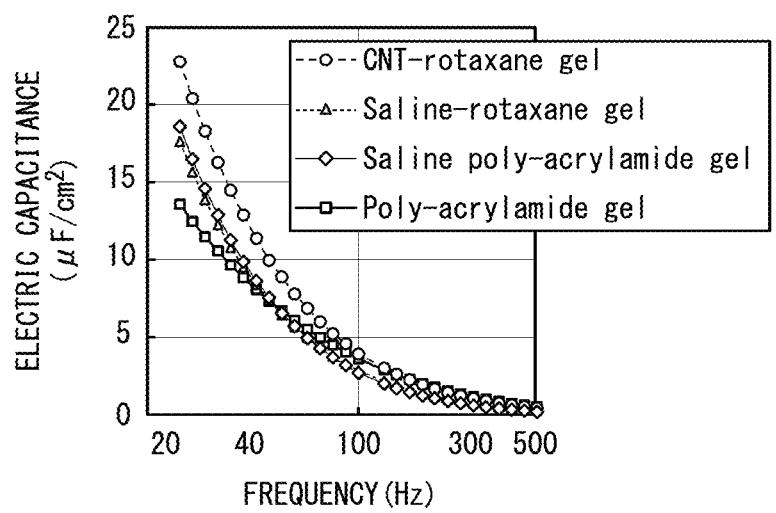
FIG. 8 is a graph showing the electrical capacitance of the composition (or a conductive material) which can be used in the electronic contact material of the multi-point probe of the invention and frequency dependency thereof

FIG. 8 is a graph showing the electrical capacitance of the composition (CNT-rotaxane gel) and the frequency dependency of the electrical capacitance. For comparison, the electrical capacitances of a polyacrylamide gel (Poly-acrylamide gel), a saline solution-containing polyacrylamide gel (Saline poly-acrylamide gel), a saline solution-containing rotaxane gel (Saline-rotaxane gel) are also indicated.

The composition (CNT-rotaxane gel) was obtained under the same conditions as the production conditions of the composition shown in FIG. 1A. The size of it was 1 cm×1 cm, and the thickness of it was 1 mm.

The polyacrylamide gel (Poly-acrylamide gel) was obtained by adding 1 mg of a photo-crosslinking agent to 300 mg of polyacrylamide, dissolving the mixture in 100 ml of deionized water, and then photo-crosslinking the solution by using UV rays. The size of it was 1 cm×1 cm, and the thickness of it was 1 mm.

The saline solution-containing polyacrylamide gel (Saline poly-acrylamide gel) was obtained by adding 1 mg of a photo-crosslinking agent to 300 mg of polyacrylamide, dissolving the mixture in 100 ml of saline solution, and then photo-crosslinking the solution by using UV rays. The size of it was 1 cm×1 cm, and the thickness of it was 1 mm.

The saline solution-containing rotaxane gel (Saline-rotaxane gel) was obtained by adding 1 mg of a photo-crosslinking agent to 300 mg of rotaxane gel, dissolving the mixture in 100 ml of saline solution, and then photo-crosslinking the solution by using UV rays. The size of it was 1 cm×1 cm, and the thickness of it was 1 mm.

As shown in FIG. 8, it can be seen that the electrical capacitance of the composition is higher than those of the gels of the related art.

In addition, when an electrical signal is detected by capacitive coupling, the strength thereof is proportional to the surface area of the electrode. When an electrical signal is detected by capacitive coupling by using an electrode which is formed from the composition, the composition is far more flexible than a metal electrode of the related art, and the electrode can be closely attached onto a biological tissue and thus has a large substantial contact area. Therefore, the detection sensitivity at a substantial capacity for obtaining an electrical signal is extremely higher than that of a metal electrode of the related art, and thus high detectability can be obtained even in a small electrode.

In addition, the composition or the conductive material includes the carbon nanomaterial, and the carbon nanomaterial, particularly, the carbon nanotubes have a high specific surface area. Therefore, even from this point of view, high signal detectability can be obtained. In addition, the conductivity of an electrode, which is manufactured from the composition or the conductive material according to the present invention, is lower than that of an Au electrode. However, when a signal is detected by capacitance, it is important that an effective surface area, rather than the conductivity, is large.

Hereinafter, the method of manufacturing the conductive material will be described with reference to FIG. 5 by using an example in which carbon nanotubes are used as the carbon nanomaterial, N, N-diethyl-N-methyl-N-(2-methoxyethyl)ammonium tetrafluoroborate ($DEMEBF_4$) is used as the ionic liquid, and polyrotaxane is used as the water-soluble polymer.

(1) First Step

First, carbon nanotubes, $DEMEBF_4$, and water are mixed with each other and stirred to prepare a first dispersion system in which the carbon nanomaterial covered with the molecules constituting the ionic liquid is dispersed.

In the rinsing step, $DEMEBF_4$ which is not bonded to the carbon nanotubes may be removed by rinsing the first dispersion system by using, for example, saline solution, ethanol, or liquid which does not destroy gel.

In this dispersion system, the carbon nanotubes covered with the molecules constituting the ionic liquid are dispersed in water. Depending on the carbon nanotubes and the amount of the ionic liquid, the dispersion system may further include: carbon nanotubes (including bundles of carbon nanotubes) which are not sufficiently covered or are not covered at all with the molecules constituting the ionic liquid; and the molecules constituting the ionic liquid.

In this step, it is preferable that the carbon nanotubes be pulverized by applying a shearing force thereto by using a jet mill or the like. Due to this step, the degree of bundling (aggregation) is decreased, and the bundles which are formed due to the Van der Waals force can be separated into individual carbon nanotubes.

Figure 11:
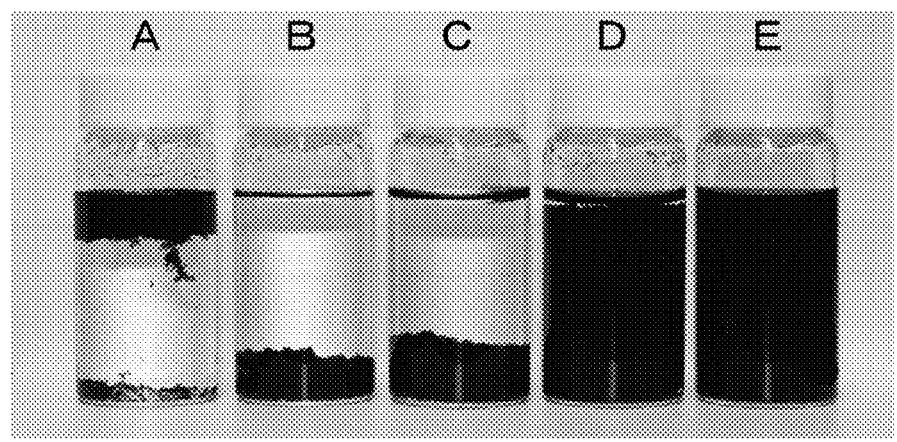
FIG. 11 is an image showing results of investigating the dispersibility of carbon nanotubes, in which (A) is an image showing a state after carbon nanotubes were put into deionized water and were stirred for 1 week, (B) is an image showing a state after carbon nanotubes and $DEMEBF_4$ were put into deionized water and were stirred for 1 week in the same manner, (C) is an image showing a state after carbon nanotubes were put into deionized water, were stirred for 1 week in the same manner, and were processed with a jet mill, (D) is an image showing a state after carbon nanotubes and 60 mg of $DEMEBF_4$ were put into deionized water, were stirred for 1 week in the same manner, and were processed with a jet mill, and (E) is an image showing a state after carbon nanotubes, $DEMEBF_4$, and microfibrillated cellulose were put into deionized water and were stirred for 1 week in the same manner to obtain a paste, and the paste was processed with a jet mill.

FIG. 11 shows the results of investigating the dispersibility of carbon nanotubes. (A) shows a state after 30 mg of carbon nanotubes were put into deionized water at 25° C. and were stirred with a magnetic stirrer at a rotating speed of 700 rpm or higher for 1 week; (B) shows a state after 30 mg of carbon nanotubes and 60 mg of $DEMEBF_4$ were put into deionized water at 25° C. and were stirred for 1 week in the same manner; (C) shows a state after 30 mg of carbon nanotubes were put into deionized water at 25° C., were stirred for 1 week in the same manner, and were processed with a high-pressure jet-milling homogenizer (60 MPa; Nano-Jet Pal, JN10, Jokoh); (D) shows a state after 30 mg of carbon nanotubes and 60 mg of $DEMEBF_4$ were put into deionized water at 25° C., were stirred for 1 week in the same manner, and were processed with a high-pressure jet-milling homogenizer; and (E) shows a state after 30 mg of carbon nanotubes, 60 mg of $DEMEBF_4$, and microfibrillated cellulose (100 mg of an aqueous solution containing 10% cellulose, "Celish (trade name)", manufactured by Daicel Chemical Industries, Ltd.) were put into deionized water at 25° C. and were stirred for 1 week in the same manner to obtain a paste, and the paste was processed with a high-pressure jet-milling homogenizer. The images were taken 1 week after the completion of stirring. "Celish (trade name)" is cellulose nanofiber which is obtained by microfibrillating a raw material of highly refined pure plant fiber by using a special processing method. Due to this processing, the raw material fiber is split into several tens of thousand pieces and is pulverized such that the thickness of the fiber is 0.1 µm to 0.01 µm.

It can be seen that (D) and (E) show high dispersibility of the carbon nanotubes in water. It can be seen that, in order to obtain high dispersibility, it is preferable that bundles of carbon nanotubes be pulverized by applying a shearing force thereto.

(2) Second Step

Next, the first dispersion system, polyrotaxane ("photo-crosslinkable gel", manufactured by Advanced Softmaterials Inc.), and water are mixed with each other and are stirred to prepare a second dispersion system in which the carbon nanomaterial covered with the molecules constituting the ionic liquid and the water-soluble polymer are dispersed.

In the rinsing step, $DEMEBF_4$ which is not bonded to the carbon nanotubes may be removed by rinsing the second dispersion system by using, for example, saline solution, ethanol, or liquid which does not destroy gel.

Figure 9:
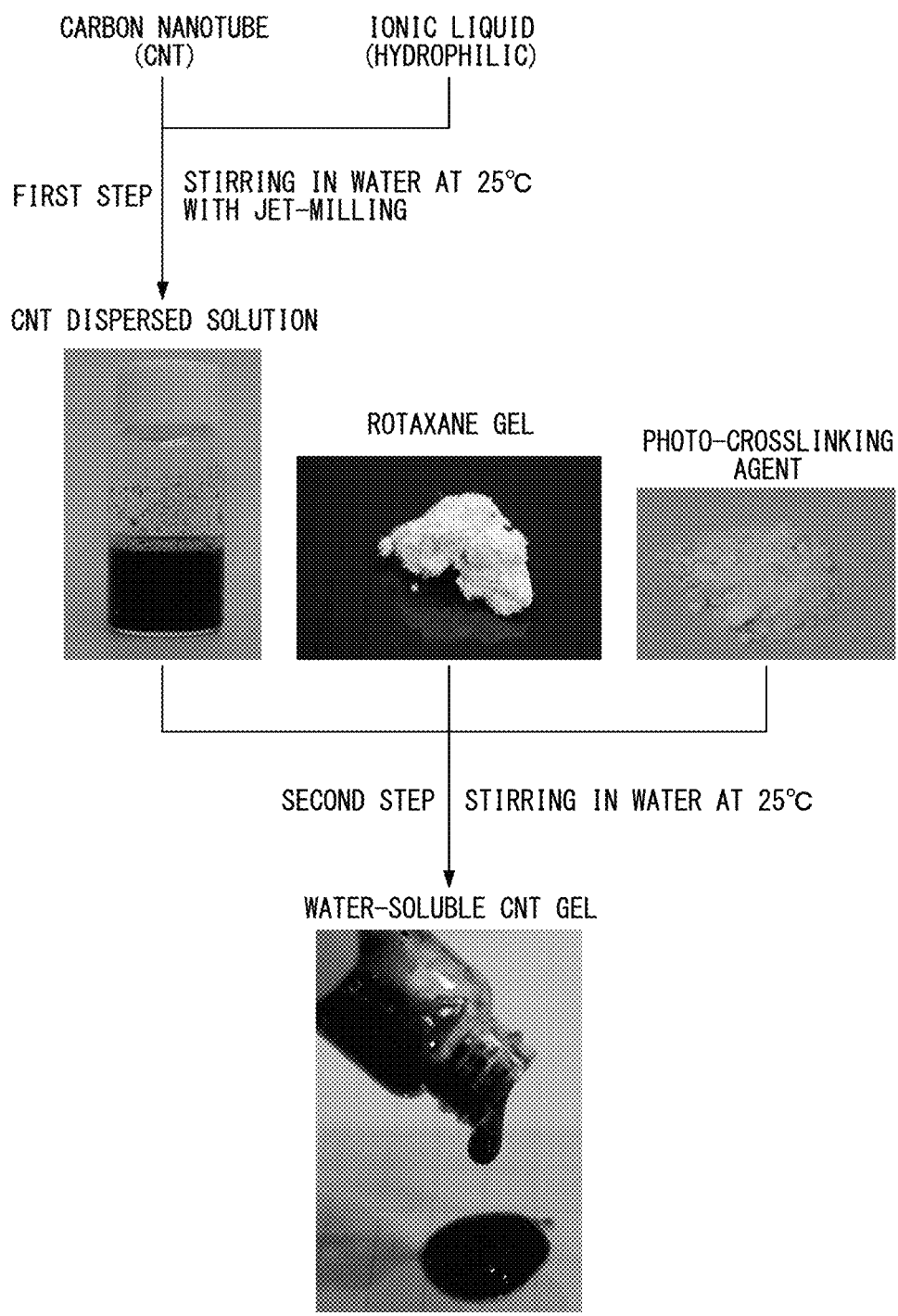
FIG. 9 is a flowchart showing a method of manufacturing a conductive material which can be used in the electronic contact material of the multi-point probe of the invention.

When the obtained composition is crosslinked as shown in FIG. 5, a crosslinking agent is further mixed. As a result, the obtained second dispersion system is a gel material as shown in FIG. 9.

(3) Crosslinking Step

Next, polyrotaxane is crosslinked, and the carbon nanotubes, which is covered with the molecules constituting $DEMEBF_4$, are dispersed in a polyrotaxane medium to obtain a composition (conductive material) in which polyrotaxane is crosslinked.

In the rinsing step, $DEMEBF_4$ which is not bonded to the carbon nanotubes may be removed by rinsing the obtained composition (conductive material) by using, for example, saline solution, ethanol, or liquid which does not destroy gel.

Through the above-described steps, the composition (conductive material) can be obtained.

Next, an example of a step of using the above-described second dispersion system to form a sheet which is formed of the composition (conductive material) according to the embodiment of the present invention or to form a line having a fine width which is formed of the composition (conductive material) according to the embodiment of the present invention will be described.

Figure 10:
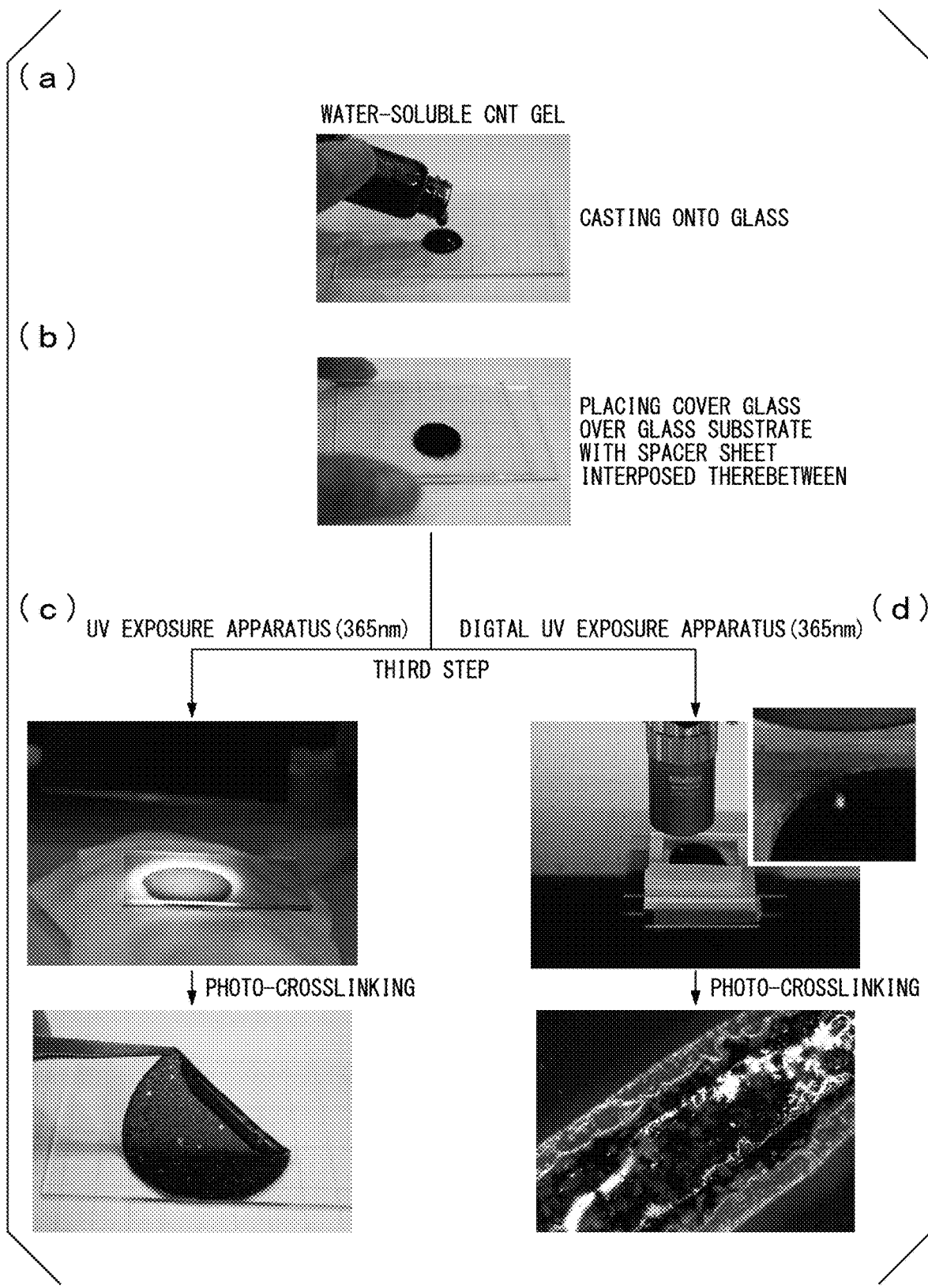
FIG. 10 is a flowchart showing an application example of the method of manufacturing a conductive material which can be used in the electronic contact material of the multi-point probe of the invention.

As shown in FIG. 10 (a), the second dispersion system is cast onto a glass substrate. Next, as shown in FIG. 10 (b), a cover glass is placed over the glass substrate with a spacer sheet having a desired thickness (in an example of the drawing, 50 µm) interposed therebetween.

Next, in order to form a sheet, the glass substrate is exposed to, for example, ultraviolet rays (365 nm) by using an ultraviolet exposure apparatus as shown in FIG. 10 (c). As a result, a sheet having a thickness of 50 µm can be obtained. In addition, in order to form a line having a fine width, the glass substrate is exposed to, for example, ultraviolet rays (365 nm) by using a digital ultraviolet exposure apparatus as shown in FIG. 10 (d). As a result, a line having a width of 50 µm can be formed.

(Multi-Point Probe Array)

Figure 12:
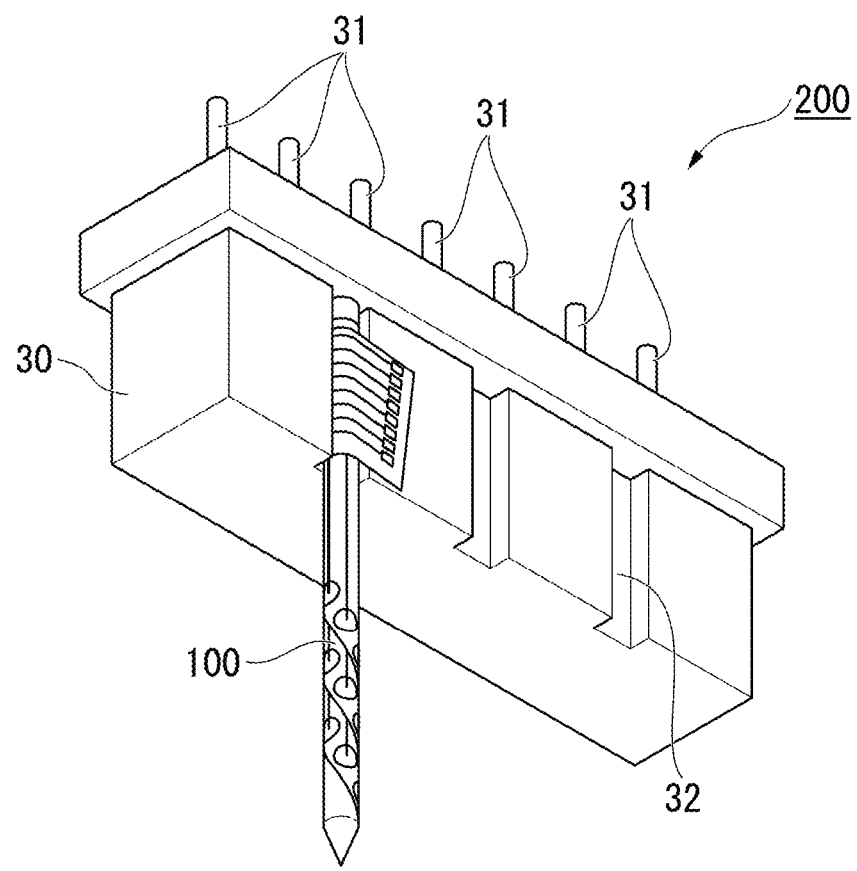
FIG. 12 is a perspective view showing an example of a multi-point probe array according to one embodiment of the invention.

FIG. 12 is a perspective view showing an example of a multi-point probe array according to one embodiment of the invention.

In a multi-point probe array 200, the plurality of multi-point probes 100 described above are provided on a base substrate 30 to stand apart from each other. In FIG. 5, six multi-point probes 100 are installed to stand, but only one multi-point probe is shown in the drawing for convenience.

In the multi-point probe 100, the vicinity of the other end 10b of the electronic contact sheet 10 is not wound, in order to easily connect an external circuit to the pads. The multi-point probe 100 is installed to stand by inserting the other end 20c of the core 20 to a groove 32 provided on the base substrate 30.

As the material of the base substrate 30, ceramics or glass epoxy having workability such as zirconia is preferably used, and a single crystal silicon substrate or a glass substrate can be used. The grooves 32 for accurately positioning the multi-point probes 100 are provided on the base substrate. The multi-point probes 100 are fit to the grooves 32, and the pads and mounting terminals (not shown) which are formed corresponding thereto are electrically connected on the base substrate 30 in a positioned state, so that the pads formed on the other end of the electronic contact sheet 10 faces the base substrate 30 side. The mounting terminals are electrically connected to electrical connectors 31 fixed to the base substrate 30 through wirings formed on the base substrate 30.

In addition, the pads of the electronic contact sheet 10 and flexible cables may be directly connected to each other, without forming the wiring or the electrical connectors 31 onto the base substrate 30.

In this case, the end portion of the electronic contact sheet 10 is adhered and fixed in a wound state so that the pads face the upper surface from the base substrate.

(Multi-Point Probe Manufacturing Method)

Hereinafter, an example of a multi-point probe manufacturing method according to one embodiment of the invention will be described.

First, the sheet-shaped insulating base material having a predetermined shape is prepared. Specifically, for example, a commercially available polyimide film or a polyethylene naphthalate film is prepared.

Next, the plurality of electronic contacts, the plurality of wirings connected to the electronic contacts, and the plurality of pads connected to the wirings are formed on one surface of the sheet-shaped insulating base material, using a well-known technology for creating a circuit. As a well-known technology for creating a circuit, a technology for creating a flexible printed wiring board is used, for example.

Next, a layer formed of the first insulating material is formed on the substrate where the circuit is formed, so that the electronic contacts and the pads are exposed.

Next, the first end of the electronic contact sheet is fixed to and started to be wound around the outer peripheral surface of the core using a cyanoacrylate adhesive, and then, a front surface and a rear surface of the electronic contact sheet are mounted using an epoxy adhesive by winding once and continuing to be wound, and a rear surface of the second end of the electronic contact sheet is finally adhered to the front surface of the electronic contact sheet using an epoxy adhesive in the same manner, and the winding is completed.

Then, the second insulating material such as Parylene covers the entire electronic contact sheet, and the second insulating material on the electronic contacts and the pads is removed using a laser or the like, to expose the electronic contacts and the pads.

It is possible to manufacture the multi-point probe generally by the steps described above.

(Manufacturing Method of Multi-Point Probe Array)

Figure 13:
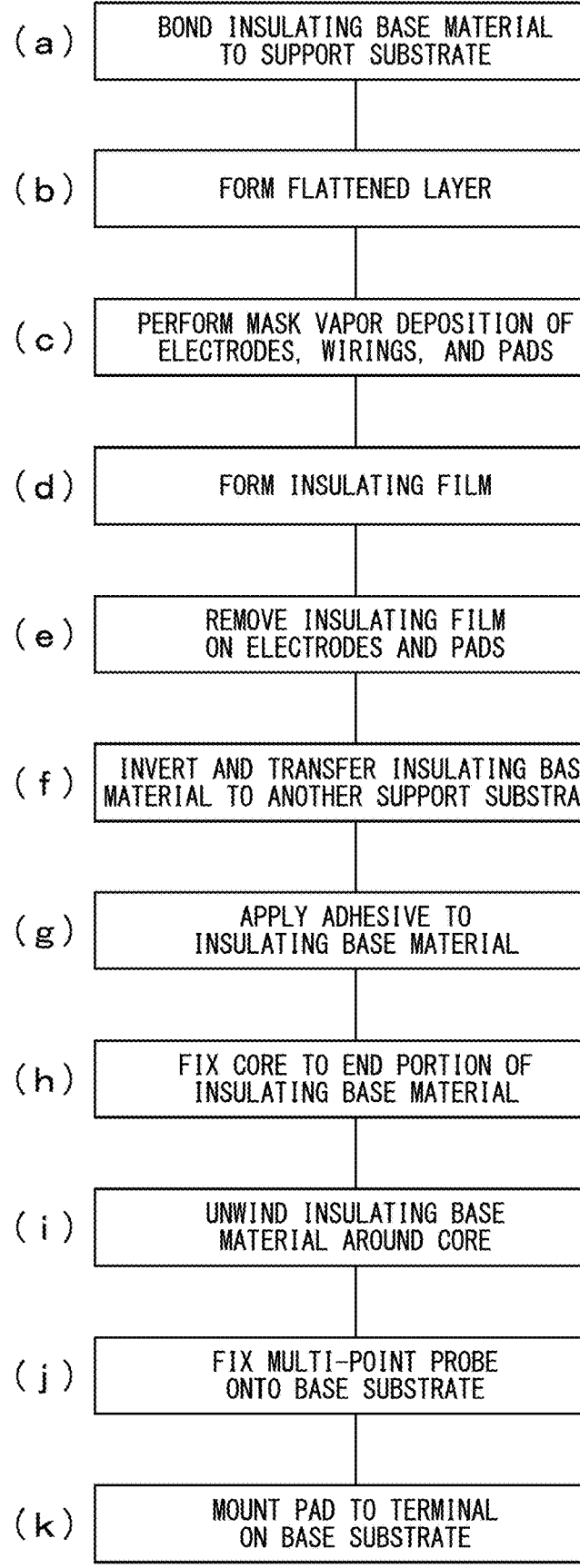
FIG. 13 is a flowchart of manufacturing steps of the multi-point probe array according to one embodiment of the invention.

An example of a manufacturing method of the multi-point probe array according to one embodiment of the invention will be described using a flowchart of manufacturing steps shown in FIG. 13. A part of steps of the manufacturing method may be applied to the manufacturing method of the multi-point probe and a part of steps of the manufacturing method of the multi-point probe described above may be applied to the manufacturing method of the multi-point probe array described below.

First, the sheet-shaped insulating base material such as a polyimide film is bonded to a support substrate such as a flat glass substrate ((a) step).

A flattened layer using Parylene by CVD is formed on one surface of the sheet-shaped insulating base material, for example ((b) step).

The plurality of electronic contacts, the plurality of wirings connected to the electronic contacts, and the plurality of pads connected to the wirings are formed on the flattened layer by mask vapor deposition, and the electronic contact sheet is manufactured ((c) step).

The entire electronic contact sheet including a circuit formed thereon is covered with the first insulating material ((d) step), and then, the first insulating material on the electronic contacts and the pads is removed ((e) step).

The sheet-shaped insulating base material (electronic contact sheet) is inverted and transferred to another support substrate ((f) step), and an adhesive such as a cyanoacrylate adhesive is applied to a first end of the surface on a side bonded to the support substrate described above ((g) step).

The core is fixed to a portion of the electronic contact sheet where the adhesive is applied ((h) step), the electronic contact sheet is wound around the core, the rear surface of a second end of the electronic contact sheet is finally adhered to the front surface of the electronic contact sheet using an epoxy adhesive in the same manner, and winding is completed ((i) step).

The second insulating material such as Parylene covers the entire electronic contact sheet, and the second insulating material on the electronic contacts and the pads is removed using a laser or the like, to expose the electronic contacts and the pads, and the multi-point probe is manufactured.

The multi-point probe is fixed to the groove of the base material ((j) step).

The pad of the multi-point probe is mounted on a terminal of the base material ((k) step).

It is possible to manufacture the multi-point probe array generally through the steps described above.

Hereinabove, the desired embodiments of the invention have been described, but the invention is not limited to the embodiments. It is possible to perform addition, omission, replacement, and modification of the configuration in a range not departing from a gist of the invention. The invention is not limited by the above description and is only limited by attached claims.

REFERENCE SIGNS LIST 1 sheet-shaped insulating base material, 1a one surface, 1c edge portion, 2 electronic contact, 3, 3a, 3b, 3c wiring, 4 pad, 10 electronic contact sheet, 10a first end, 10b second end, 20 core, 20a outer peripheral surface, 20b one end, 20c other end, 30 base substrate, 100 multi-point probe, 200 multi-point probe array

What is claimed is:

1. A multi-point probe comprising:
a probe; and
an electronic contact sheet adapted to wind around the probe, wherein the electronic contact sheet comprises:
a base formed from an insulating sheet comprising a distal edge, a proximal edge, a first lateral edge parallel to a longitudinal axis of the probe and a second lateral edge parallel to and opposite from the first lateral edge, wherein the distal edge recedes from the first lateral edge to the second lateral edge;
a plurality of electronic contacts separated from each other and arranged along a distal portion of an upper surface of the base; and
a plurality of wirings, wherein each of the plurality of wirings are connected to a corresponding plurality of electronic contacts and extends from a first end towards a second end; and
wherein when the electronic contact sheet winds around the probe, the electronic contact sheet forms a tubular shape having multiple layers so that the plurality of electronic contacts are arranged spirally along the longitudinal axis and are exposed to an external environment; and
wherein the plurality of wirings other than an uppermost layer of the multiple layers are covered with another layer of the multiple layers.

2. The multi-point probe according to claim 1, wherein the plurality of wirings are extended along the longitudinal axis over a predetermined range using the plurality of electronic contacts as a starting point.

3. The multi-point probe according to claim 1, further comprising a plurality of pads which are connected to each of the second end of the plurality of the wirings and configured to connect to an external circuit.

4. The multi-point probe according to claim 3, wherein the plurality of wirings are covered with a first insulating material so that the plurality of electronic contacts and the plurality of pads are exposed.

5. The multi-point probe according to claim 4,
wherein a first shielding conductive layer is formed on a bottom surface of the base.

6. The multi-point probe according to claim 5,
wherein a second shielding conductive layer is formed on the upper surface of the base where the plurality of wirings are arranged.

7. The multi-point probe according to claim 1, further comprises an amplifier connected to the plurality of electronic contacts.

8. A multi-point probe array, wherein the plurality of multi-point probes according to claim 1 are provided on a base substrate and arranged to stand apart from each other.

9. An electronic contact sheet according to claim 1.

10. A manufacturing method of the multi-point probe according to claim 4,
winding the first lateral end towards the second lateral end so that the plurality of electronic contacts are exposed;
coating the second insulating material on the entire electronic contact sheet; and
removing the second insulating material disposed on the plurality of electronic contacts and the plurality of pads.

\* \* \* \* \*